United States Patent
Panasyuk

(10) Patent No.: US 7,943,764 B2
(45) Date of Patent: May 17, 2011

(54) METHOD FOR PRODUCING SULPHATED GLYCOSAMINOGLYCANS FROM BIOLOGICAL TISSUES

(75) Inventor: Andrey Fedorovich Panasyuk, Moscow (RU)

(73) Assignees: Dimitry Alekseevich Savaschuk, Leninsky Raion, Moskovskaya Obl. (RU); Andrey Fedorovich Panasyuk, Moscow (RU)

( * ) Notice: Subject to any disclaimer, the term of this patent is extended or adjusted under 35 U.S.C. 154(b) by 221 days.

(21) Appl. No.: 12/091,707

(22) PCT Filed: Oct. 27, 2005

(86) PCT No.: PCT/RU2005/000525
§ 371 (c)(1),
(2), (4) Date: Apr. 25, 2008

(87) PCT Pub. No.: WO2007/049987
PCT Pub. Date: May 3, 2007

(65) Prior Publication Data
US 2008/0262218 A1    Oct. 23, 2008

(51) Int. Cl.
*C07H 5/10* (2006.01)
(52) U.S. Cl. ........................... 536/122; 536/127
(58) Field of Classification Search .................. None
See application file for complete search history.

(56) References Cited

U.S. PATENT DOCUMENTS

| 3,895,106 A | 7/1975 | Morrison |
| 3,895,107 A | 7/1975 | Morrison |

FOREIGN PATENT DOCUMENTS

| DE | 2037942 A  | 11/1971 |
| GB | 1344727 A  | 4/1971  |
| RU | 2056851 C1 | 3/1996  |
| RU | 2056851 C1 * | 3/1996 |
| RU | 2118524    * | 9/1998 |
| RU | 2118524 C1 | 9/1998  |
| RU | 2139715 C1 | 10/1999 |

OTHER PUBLICATIONS

Adams, Mark and Muir, Helen, Biochem J. "The glycosaminoglycans of canine menisci", vol. 197, pp. 385-389 (1981).*
Stamatoglou, Stamatis and Keller, John, The Journal of Cell Biology "Correlation between Cell Substrate Attachment In Vitro and Cell Surface Heparan Sulfate Affinity for Fibronectin and Collagen", vol. 96, pp. 1820-1823 (1983).*
Grinnell, Frederick and Bennett, Marylyn, J. Cell. Sci. "Fibroblast Adhesion on Collagen Substrata in the Presence and Absence of Plasma Fibronectin", vol. 48, pp. 19-34 (1981).*
Google Search results for "sterilize dermatan sulfate", hit 2, publication date of article Aug. 2003.*
Amersham Biosciences "Dextran Sulphate sodium salt", p. 1-4 (for publication date, see p. 1 of Non-Patent Documents on PTO-892, entry X).*
International Search Report in PCT/RU2005/000525, dated Jul. 6, 2006, corresponding to the present application.

* cited by examiner

*Primary Examiner* — Shaojia Anna Jiang
*Assistant Examiner* — Bahar Schmidtmann
(74) *Attorney, Agent, or Firm* — Abelman, Frayne & Schwab

(57) ABSTRACT

A method for isolating sulphated glycosaminoglycans washes a mechanically cleaned tissue, exposes tissue in a solution of 0.1M phosphate pH 5.8-6.0 buffer heated to a temperature of 65° C. for 30 minutes, overcooks the tissue in activated 0.1-0.4% papain at 65° C. for 6-24 hours, cools the papain digest to 4° C., removes fats and undigested tissue residues, selectively isolates the sulphated glycosaminoglycans for 4-10 hours on a solid carrier, obtained from bone tissue collagen with particle sizes ranging from 0-01 to 0.35 cm3, washes the carrier with 0.05-0.1 N-hydrochloric acid, degreases and eluates the carrier with a solution of 0.6-0.15 N-mineral salt in 0.8 N-acetic acid or in 0-01-0-025 N-alkali liquor, precipitates the sulphated glycosaminoglycans with ethanol, centrifuges with 1500 r.p.m. for 15 minutes at a temperature of 4° C., washes the precipitate with ethanol or acetone, and dries and sterilizes the precipitate.

12 Claims, No Drawings

US 7,943,764 B2

METHOD FOR PRODUCING SULPHATED GLYCOSAMINOGLYCANS FROM BIOLOGICAL TISSUES

CROSS-REFERENCE TO RELATED APPLICATIONS

This application is a 371 of international application number PCT/RU2005/000525, filed on Oct. 27, 2005.

BACKGROUND OF THE INVENTION

1. Field of the Invention

This invention covers the field of medicine and can be used for obtaining of major constituents of connective tissues including sulphated glycosaminoglycans (sGAG) for application as pharmaceutical substances in medicine and veterinary medicine, drugs and preventive materials, e.g. eye drops, ointments, suspensions etc. or in the composition of medical products.

2. Description of the Related Art

A method of obtaining sGAG from the trachea of cattle and shark's fins including the hydrolysis of an acetone powder suspension from tissues with 1% papain solution for 24 hours at 62° C., the subsequent precipitation of hydrolyzate with acetone, sediment dissolution in saline, decoloration with use of $KMnO_4$ and precipitation with acetone (DE 2037942, A61K31/725) is known.

However, this method is simple and convenient enough, but it does not obtain a high-purity sGAG preparation. Moreover, this method does not ensure high recovery of sGAG and its realization is very expensive.

A method of extraction of sulphated glycosaminoglycans from the cornea including the treatment of the cornea of farm livestock with water solutions and ethanol with the subsequent boiling (RU 2056851) is known.

The disadvantage of this method is a partial loss of glycosaminoglycans, such that a part of the glycosaminoglycans remains in the sediment by dialysis, in particular keratan sulfate. Furthermore, a part of the glycosaminoglycans remains in the non-destroyed tissue by enzymatic treatment of the cornea, which leads to the reduction of end product output, and only solute sulphated glycosaminoglycans can be obtained with use of this method.

A method of extraction of glycosaminoglycans from fibrous cartilage is known, by which a tissue sample is exposed to enzyme proteolysis, specific components of glycosaminoglycans are extracted from the obtained hydrolyzate by precipitation of them from the hydrolyzate by quaternary ammonium bases or detergents and their stepwise purification and quantification is carried out (Adams N. E. Muir H. The glycosaminoglycans of canine menisci/Biochem. J. 1981. Vol. 197, No. 2. P. 385-389).

A method of extraction of glycosaminoglycans from tissues forming elements of a joint including the fibrous cartilage is also known, which consists in enzyme proteolysis of a minced tissue sample in 0.1 M acetate buffer containing papain in a quantity of one fourth of fresh weight at the temperature of +60±4° C. for 24 hours, deproteinization of the hydrolyzate obtained by the trichloroacetic acid for 24 hours at the temperature of +4° C., purification of extracted glycosaminoglycans with the help of their precipitation with ethanol containing calcium acetates or sodium acetates for 24 hours at the temperature of +4° C., and quantification of glycosaminoglycans (E. V. Karyakina. D. V. Kosyagin. Features of extraction of glycosaminoglycans from tissues forming elements of a joint/The All-Union Rheumatologists Conference: Lecture theses (Dec. 7-9, 1988). Moscow, 1988, P. 108-109).

The disadvantage of the known methods is a long duration of study (4-5 days), which does not allow the obtaining of current information on the state of intra-articular structures of connective tissue.

A method of obtaining of sulphated glycosaminoglycans is known, which consists in the treatment of the cornea of farm livestock with water solutions and ethanol with the subsequent boiling, in that the corneas of farm livestock are put into the half-and-half mixture of saline and distilled water with the ratio of the cornea and water mixture 1:1, frozen repeatedly three times at 0° C., reduced to fine particles of 0.1×0.1 mm, then ethanol is added in concentration of 1%, the mixture is homogenized, ethanol is added repeatedly to the final concentration of 5%, and then the mixture is boiled for 5-10 minutes. (RU 2118524, A61F9/00 A61K35/14 publ. Sep. 10, 1998).

The disadvantage of the mentioned method consists in the laborious expensive treatment, which does not provide for full output and liberating of sGAG from the solution, and also in impurities of protein and other antigenic molecules being present in the mentioned tissues, which sufficiently reduces the purity of the end product.

This method of obtaining sGAG from the cornea is selected as a prototype, as it the most closely relates to the invention proposed with respect to its technical decision.

BRIEF SUMMARY OF THE INVENTION

The goal of this invention is the improvement of the quality of sGAG extraction for application in biochemistry, for obtaining pure complex polysaccharides and also pharmaceutical substances by means of the enzyme treatment of biological tissues, extraction of sGAG on a collagen carrier of the bone tissue and their purification and, as a result of realization of these steps, increased output of the high-quality product, reduction of protein quantity in the preparation, reduction of its antigenicity and an increase of its biocompatibility.

The technical result reached by use of this invention is the obtaining of high-purity sGAG for obtaining pharmaceutical substances, which can be widely used for obtaining pharmaceutical preparations and a series of goods of medical purpose, in which the composition of sGAG are included.

The technical result is reached by the method of obtaining sGAG which consists in the following according to this invention: the biological tissue reduced to small particles is washed in a buffer solution heated to 65° C., treated by an enzyme under specific conditions, fats and tissue remainders are removed from the digest, sGAG on a collagen carrier of the bone tissue is selectively extracted, eluated from the carrier with a sodium chloride solution in an acetic acid or with weak alkali solutions, precipitated with organic solutions, dried and sterilized.

DETAILED DESCRIPTION OF THE INVENTION

The present invention is related to international application number PCT/RU2005/000525, filed on Oct. 27, 2005, which is incorporated herein by reference in its entirety.

The raw material for sGAG can be any tissues of natural origin (animals or human donor tissue, if necessary) containing proteoglycans (cornea, cartilage, bone, trachea, liver, small intestine etc.). It is known that proteoglycans contain sGAG, such as chondroitin sulfates, keratan sulfates, heparan sulfates and dermatan sulfates. In addition, heparin not connected with the protein in the organism's tissues belongs to sGAG. The first ones in the composition of proteoglycans are connected with hyaluronic acid with core proteins characterized by a high antigenicity (M. Stacy and S. Barker "Carbohydrates of living tissue" M, Mir, 1965, P. 35-38).

The sGAG technology requires an initial mechanical treatment of tissue, when the tissue is first cleaned from remainders of soft tissues and blood. Then the tissue is grinded: soft tissues are minced in the frozen state, hard tissues, e.g. cartilage or bone are cut or sawn into fragments.

A sufficient inventive feature is that that the tissue reduced to small particles is washed twice with the 0.1 M phosphate buffer heated to 65° C. with pH 5.8-6.0 in proportion of 1 part of tissue to 1.5-2 volume of the buffer and then kept exposed in new portion of the heated buffer for 15-30 minutes. This stage allow optimization of conditions for further action of the enzyme upon the digest tissue, providing a significant increase in the yield of sGAG and a reduction of tissue incubation periods under conditions of the increased temperature, herewith providing a greater safety of the product obtained.

The washed tissue is exposed to enzymatic hydrolysis at 65° C. for 6-24 hours. A 0.1-0.4% solution of the activated papain, which, as it is well-known, destroys proteins and liberates polysaccharide chains of sGAG from proteoglycans under these conditions, was used as an enzyme decomposing the tissue antigens such as proteins, glycoproteins and proteoglycans. Therefore, the polysaccharide chains of sGAG are fully maintained. The papain concentration of 0.1-0.2% is optimal for most types of connective tissues (cornea, sclera, small intestine, lung) at the temperature of digesting mode 65° C. and incubation time of 6 hours. However, this concentration must be increased to 0.3 to 0.4% and the digest time to 24 hours by treatment of harder and thicker tissues, such as trachea or bone.

The tissue digest obtained in such a way is cooled to 4° C. and kept at this temperature for 2-24 hours. The precipitation of tissue remainders and solidification of lipids which are then removed by filtering in the cold occurs at this temperature and incubation time. Undigested tissue remainders (e.g. bones) are then washed with equal volume of distilled water heated to 60-80° C., which is then added to the base digest. This stage is necessary for loss reduction of sGAG by their subsequent extraction.

The efficiency of enzyme action upon the material is determined by output to a digest of sGAG, namely, by their coloration with 1.9-dimethylene blue with the subsequent spectrophotometric evaluation at the wave length of 535 nm (Farndel's method).

A sufficient inventive feature is also that that sGAG is selectively extracted on a collagen carrier of the bone tissue with the particle size from 0.01 to 0.35 $cm^3$, preferably 0.125 $cm^3$. It has been found experimentally by us that the bone collagen is affinely able to bind sGAG and a series of other biologically active substances. Its application as a carrier acting as a substrate for the affine chromatography is based exactly on this principle.

The bone tissue collagen meets all basic requirements made to carriers (matrixes) applied in the affine chromatography for separation, concentration and purification of bioactive substances. So, it contains many groups which can affinely bind with a ligand; it does not show any decomposition by binding with a ligand and does not lose its features by subsequent elution of biomolecules from it by acid or alkali solutions; it provides quick and uniform flow of the solution; and it poorly reacts or does not react at all with other macromolecules under certain circumstances. Sufficient plasticity and resistance to the effect of acid, alkali and saline solutions are also to be noted among the advantages of the bone tissue collagen as a carrier. Its porous fibrous structure having a large reaction surface and high binding capacity allows subsequent concentration of the ligand and, as a consequence of this, an increased output of the purified end product.

A material for obtaining of a hard carrier is a spongy bone of mammals. The collagen of this tissue consists of the collagen of type I by 95% and is characterized by very poor solubility in acid or alkali solutions and high resistance to the action of protein-degrading enzymes.

The size of collagen pieces used as a sorbent is determined by us experimentally by extraction of sGAG on them. At that, the minimum size of a piece is equal to 0.01 $cm^3$, as it ensures the minimum useful capacity and a sufficient binding surface. The maximum size is determined as 0.35 $cm^3$, as the exceeding of this size hampers passing of circulating solutions into the carrier's pores.

The selective extraction of sGAG on the collagen carrier is carried out at room temperature for 4-24 hours. Just few hours of incubation are enough for binding of sGAG with a substrate at a low concentration of sGAG in the digest, while as a rule this time amounts to 24 hours at a high concentration. The incubation time is established experimentally according to elimination of sGAG from the incubating solution: they are not observed already in 4-10 hours of incubation at the low temperature and in 24 hours of incubation at the high temperature.

The collagen carrier is then consecutively washed first with water, then with weak acid solutions (0.05-0.1N) for removal of nonspecifically bound matters and, in particular, protein molecules. The acid concentration was determined experimentally. So, a part of nonspecifically bound proteins can remain on the collagen substrate and later on can pollute the product obtained by concentration of the hydrochloric acid lower than 0.05 N, whereas a partial removal of sGAG from the collagen substrate can occur by acid concentration more than 0.1 N. After washing of collagen with acid, it is to be washed with distilled water. The washing of the substrate is carried out until the complete elimination of the protein in the washout.

The output of the protein into the eluate was determined spectroscopically by Lowry's method of pharmacopeia at the wave length of 400 nm and according to Bradford's method at the wave length of 260 and 280 nm.

A sufficient inventive feature is that that sGAG is removed from the substrate with a 0.6-1.5 N sodium chloride solution in 0.8 N acetic acid. The destruction of a carrier does not occur by use of this mixture (salt and acid) because many proteins and especially collagen are insoluble under these conditions, while the salt concentration in the solution is optimal for removal of sGAG from the collagen carrier. It has been found experimentally by us that not all sGAG come off of the column and the time of their output increases sufficiently by salt concentration below 0.6 N and the protein content in the eluate can grow by salt concentration above 1.5 N at the expense of removal of proteins from the carrier. The application of the developed mixture allows a sufficient increase in the purity of the matter obtained and exclusion of such labor-intensive processes as dialysis against the saturated saline solution and subsequent desalination of the solution of sGAG before its precipitation with ethanol from the stage of purification of sGAG. In addition, this reduces not only expenses for reagents used but also the time for extraction of a pure product, which is very important for the commercial production of a sGAG substance.

The precipitation of sGAG from the eluate is carried out in the presence of ethanol at 4° C. for 24 hours. 2.5 parts of 95% ethanol are added to 1 part of eluate. The supernatant is removed by centrifugation at 1500 rev/min for 10 minutes. Then the sediment is washed with ethanol and dried.

A sufficient inventive feature is that that it is also possible to remove sGAG from the substrate successfully by weak (0.015 to 0.025H) alkali solutions. These can be NaOH, KOH, $Ca(OH)_2$ etc. The concentration of the alkaline solution is also determined by us experimentally and is an optimal concentration for the removal of sGAG from collagen. Not all sGAG come off of the column and the time of their output increases sufficiently by concentration of the NaOH solution below 0.015 N. The sGAG destruction process and the increase of the protein content in the eluate due to the destruction of the collagen substrate are observed by alkali concentration above 0.025 N.

The elution of sGAG must be continued in both cases until their output from the column does not stop, which is controlled by their presence in the solution according to the Farndel's method.

The solution of sGAG removed from the collagen carrier by the alkali is neutralized by the acetic acid up to pH 7.0 and then precipitation of sGAG is carried out with ethanol in the proportion of 1 part of eluate to 2.5 parts of ethanol. The precipitation is carried out by centrifugation for 10 minutes at 1500 rev/min at 4° C. The precipitation of all sGAG and their optimum maintenance occurs by this speed, time and temperature. The sediment is dried by double washing with absolute ethanol or acetone.

The sGAG powder is packed into sterile bottles immediately after drying for prevention of possible bacterial contamination. The sGAG powder obtained in this manner is sterilized with the use of a radiation method. This sterilization method is worked out experimentally, does not lead to destruction of the preparation and does not reduce its biological activity.

The comparative analysis of the quantitative and qualitative output of the obtained product has shown that the sGAG content in samples amounts to 98% and the protein content does not exceed 1.5-2%, and this significantly improves these product characteristics as compared with the prototype (3-6%).

The biological activity of obtained sGAG was determined in the environment of cell cultures and simulated animal experiments with the use of methods described by us earlier (A. F. Panasyuk, E. V. Larionov. "Chondroitin sulfates and their role in chondrocyte interchange and intercellular matrix of cartilaginous tissues". Research and practical rheumatology, 2000, No. 2, P. 46-55).

Brief Description of the sGAG Obtaining Procedure.

1 kg of pigs' tracheas is washed free from blood, slitted and frozen. The pulverized tissue is washed with 2 liters of 0.1 N phosphate buffer heated to 65° C., pH 5.8-6.0. Then the buffer is poured off and the tissue is incubated in new portion of heated 0.1 N phosphate buffer pH 5.8-6.0 for 30 minutes. Then the tissue is put into the 0.3% activated papain solution and incubated for 16 hours at 65° C. by regular stirring of the solution. After digesting the solution is cooled, filtered and let pass through a column with spongy collagen from the cattle's bone tissue with particle size 0.03-0.3 cm$^3$, preferably 0.125 cm$^3$. The incubating is carried out for 24 hours, then the collagen carrier is stepwise washed free from the incubating medium and biomolecules nonspecifically bound with the carrier first with flowing water, then with 0.1 N hydrochloric acid and with distilled water. The sGAG is then removed from the carrier with the solution of 1.0 N sodium chloride in 0.8 N $CH_3COOH$.

The sGAG is precipitated with ethanol 2.5 vol. parts of ethanol per 1 vol. part of eluate at 4° C. The sediment is separated by centrifugation at 1500 rev/min for 15 minutes, then it is washed twice with the absolute ethanol, dried, packed and sterilized.

The quantitative analysis of sGAG is conducted according to Farndel's spectrophotometric method such that the content of sGAG in the preparation is 98-99%. Protein acc. to Lowry with Bradford's modification less than 0.5%.

Consequently, these actions lead to reduction of antigenicity, as the quantity of protein reduces significantly as compared with the selected prototype. The proposed method of treatment allows for obtaining minimum 98% output of sGAG and reduction of the substance's antigenicity due to the removal of core proteins contained in proteoglycans and this increases the biocompatibility of this material and reduces the number of complications by its application as a drug or within the composition of goods of medical purpose.

The invention is explained by examples of a specific execution for a better insight of the essence of the present invention.

Example 1

Obtaining of sGAG from pigs' corneas. 1 kg of pigs' corneas is cleaned from mechanical impurities, washed free from blood, slitted and frozen. The pulverized tissue is washed with 2 liters of 0.1 N phosphate buffer heated to 65° C., pH 5.8-6.0 and then the corneas are put in new portion of heated 0.1 N phosphate buffer pH 5.8-6.0 for 15 minutes. Then the buffer is poured off and the tissue is put into the 0.2% activated papain solution and incubated for 8 hours at 65° C. After digesting of tissue the solution is cooled to room temperature and filtered. The cleaned solution is passed through a column with a collagen carrier obtained from the cattle's bone tissue. The particle size can vary within the limits of 0.03-0.35 cm$^3$. The incubating is carried out for 20 hours, then the collagen carrier is stepwise washed free from the incubating medium and biomolecules nonspecifically bound with the carrier first with flowing water, then with 0.05 N hydrochloric acid and with distilled water. The sGAG is then removed from the carrier with the solution of 1.5 N sodium chloride in 0.8 N $CH_3COOH$ and precipitated with ethanol 2.5 vol. parts of ethanol per 1 vol. part of eluate at 4° C. The supernatant is separated by centrifugation at 1500 rev/min for 10 minutes, then the sediment is washed twice with the acetone, dried, packed and sterilized.

The quantitative analysis of sGAG conducted according to Farndel's spectrophotometric method showed that the content of sGAG in the preparation is 98.5%.

Protein acc. to Lowry with Bradford's modification was 0.85%.

Concentration of extracted sGAG was 5.0 mg/g of fresh weight.

According to the prototype, concentration of sGAG was 4.23 mg/g of fresh weight.

The obtained preparation of sGAG calculated based on the dry weight contains:

| | |
|---|---|
| Hexosamine | 29-37% (determined as 5); |
| Hexuronic acids | 12-14% (determined as 6); |
| Sulphate | 18-21% (determined as 7); |
| Protein | 0.5-0.9% (determined as 8). |

The mentioned data are the evidence of a fact that the chemical composition of the obtained preparation is typical for sGAG, and so the dominance of sGAG with small content of uronic acids is obvious. This indicates the presence of a large quantity of keratan sulfate in the preparation because it contains hexose, namely galactose instead of uronic acids as opposed to chondroitin sulfates.

TABLE 1

Quantification of keratan sulfate.

| | Quantity of sGAG (mg/ml) | | % sGAG | |
|---|---|---|---|---|
| | Before | With | | |
| No. | treatment | β-hyaluronidase | remained | destroyed |
| 1 | 0.34 | 0.22 | 64.7 | 35.3 |
| 2 | 0.35 | 0.23 | 65.7 | 34.3 |
| 3 | 1.18 | 0.75 | 63.6 | 36.4 |
| 4 | 1.72 | 1.20 | 69.8 | 30.2 |
| | | | 66.0 ± 1.4 | 34.0 ± 1.4 |
| | | | Keratan sulfate | Chondroitin sulfate |

So, after pretreatment of the preparation with β-hyaluronidase (determined as 9), which hydrolyzes chondroitin sulfates only, the content of sGAG in the preparation was determined once again. It appears (see Table 1) that the preparation obtained with use of the proposed method represents a mixture of chondroitin sulfates and keratan sulfate in proportion of 1:2. The latter completely corresponds to published scientific data on sGAG content in the cornea tissue.

Thus, the proposed procedure leads to the increased end product output, improvement of its quality and reduction of antigenicity, as the protein quantity is significantly reduced as compared with the selected prototype.

Example 2

Obtaining of sGAG from pigs' lungs. 1 kg of pigs' lungs is slitted, washed free from blood with water, frozen and then homogenized. The pulverized tissue is defreezed, washed twice with 1.5 liters of 0.1 N phosphate buffer heated to 65° C., pH 5.8-6.0. The buffer is poured off and the tissue is put in a new portion of heated 0.1 N phosphate buffer pH 5.8-6.0 for 15 minutes. The washed tissue is embedded by the 0.25% activated papain solution and incubated for 12 hours at 65° C. by regular stirring. After digesting the solution is cooled to 4° C., filtered and let pass through a column with spongy collagen from the cattle's bone tissue with particle size 0.01-0.25 $cm^3$. The incubating is carried out for 16 hours, then the collagen carrier is stepwise washed free from the incubating medium and biomolecules nonspecifically bound with the carrier first with flowing water, then with 0.1 N hydrochloric acid and with distilled water. The sGAG is then removed from the carrier with the solution of 0.02 M NaOH, alkali is neutralized with the acetic acid to pH 7.0 and sGAG are precipitated with ethanol 2.5 vol. parts of ethanol per 1 vol. part of solution at 4° C. The sGAG are precipitated by centrifugation at 1500 rev/min for 10 minutes at 4° C., the sediment is washed first with ethanol, then with the acetone, dried, packed and sterilized with the use of a radiation method.

The quantitative analysis of sGAG is conducted according to Farndel's spectrophotometric method such that the content of sGAG in the preparation is 98-99%. Protein acc. to Lowry's method with Bradford's modification less than 1.5%.

These actions lead to reduction of antigenicity, as the quantity of protein reduces significantly as compared with the selected prototype.

Example 3

Obtaining of sGAG from mammals' spongy bone. The animals' spongy bone, having passed a required veterinary control, is mechanically cleaned from muscles and tendons, sawn up to plates with the thickness of 1.0 cm or mechanically destroyed up to the particle size 0.2 to 1 cm. 1 kg of sawn bone is washed twice with 1.5 liters of 0.1 N phosphate buffer heated to 65° C., pH 5.8-6.0. The buffer is poured off and the tissue is put in a new portion of heated 0.1 N phosphate buffer pH 5.8-6.0 for 20 minutes. The bone plates are put into the solution of activated 0.4% papain at 65° C. in the thermostat for 24 hours. The digest is poured off and the bone plates are washed with a multiple volume of distilled water heated to 70° C. The digest and ablution are put together, the resulting solution is cooled to 4° C. for 20 hours, filtered and passed through a column with a bone collagen with the particle size within the limits of 0.05-0.3 $cm^3$. The incubating is carried out for 24 hours, then the collagen carrier is stepwise washed free from the incubating medium and particles nonspecifically bound with the carrier first with flowing water, then with 0.1 N hydrochloric acid and with distilled water. The sGAG is precipitated from the solution in proportion of 1:2.5, the sediment is centrifuged at 1500 rev/min for 15 minutes, washed with ethanol, dried, packed and sterilized by autoclaving.

The quantitative analysis of sGAG conducted according to Farndel's spectrophotometric method showed that the content of sGAG in the preparation is 98.6%.

Protein acc. to Lowry's method with Bradford's modification was 1.2%.

Concentration of lipids was less than 1%.

Concentration of extracted sGAG was 1.84 g/kg of fresh weight.

Concentration of sGAG according to the prototype was 1.5 g/kg of fresh weight.

These actions lead to reduction of antigenicity, as the quantity of lipids and protein reduces significantly as compared with the selected prototype.

So, it is obvious that the proposed method of tissue treatment increases the output of sGAG, brings their purity to the level of 98-99% and reduces the antigenicity due to the removal of protein components containing in this tissue. The latter ensures high biocompatibility of sGAG and sharply reduces the number of complications by its application as a drug or within the composition of goods of medical purpose.

INDUSTRIAL APPLICABILITY

This invention is industrially applicable, mastered in vitro, such that the laboratory results show the practical value of the obtained pharmaceutical substance in medicine and veterinary medicine, drugs and preventive materials, e.g. eye drops, ointments, suspensions etc. or within the composition of goods of medical purpose.

What is claimed is:

1. A method for extraction of sulphated glycosaminoglycans (sGAG) from a biological tissue containing proteoglycans comprising the steps of:
   (a) mechanically cleaning and washing said tissue, and then reducing said tissue either to small particles or a thin plate, thereby to form a mechanically treated tissue;

(b) washing said treated tissue twice with 0.1 N phosphate buffer heated to a temperature of at least about 65° C. and having a pH in the range of 5.8 to 6.0; thereafter
(c) holding the washed, treated tissue in a 0.1 N phosphate buffer for a period of at least 15 minutes; then
(d) incubating the washed, treated tissue in a 0.1-0.4% solution of activated paipan, heated to a temperature of at least about 65° C., for a period of 6-24 hours, thereby obtaining a tissue digest;
(e) thereafter cooling the digest to precipitate tissue and solidify lipids;
(f) filtering the digest to remove the precipitated tissue and lipids to form a cleaned digest solution;
(g) contacting the cleaned digest solution with a hard collagen carrier, with particle size between 0.01 and 0.35 cm$^3$, for a period between 6-24 hours, in order to bind sGAG to said carrier; thereafter
(h) washing said collagen carrier with water, then a weak acid solution, and then distilled water;
(i) removing sGAG from said collagen carrier using 0.6-1.5 N mineral salt solution in 0.8 acetic acid or using 0.01 to 0.025 N alkali solution to form an eluate containing sGAG;
(j) precipitating sGAG from the eluate using ethanol; and
(k) separating the sGAG from the eluate using a centrifuge; and
(l) washing the sGAG sediment with ethanol or acetone, and then drying and sterilizing the sGAG material thus obtained.

2. The method of claim 1, wherein the 0.1 N phosphate buffer used in step (c) is new from the buffer used in step (b).

3. The method of claim 1, wherein the cooling step (e) is carried out for a period of 2-24 hours.

4. The method of claim 2, wherein the cooling step (e) is carried out at a temperature of about 4° C.

5. The method of claim 1, wherein step (g) is carried out at room temperature.

6. The method of claim 1, wherein the collagen carrier of step (g) is obtained from cattle bone.

7. The method of claim 1, wherein the collagen carrier of step (g) is spongy bone.

8. The method of claim 1, where the particle size of the collagen carrier is approximately 0.125 cm$^3$.

9. The method of claim 1, wherein sGAG is removed from said collagen carrier in step (i) using 0.6-1.5 N mineral salt solution in 0.8 acetic acid.

10. The method of claim 1, wherein sGAG is removed from said collagen carrier in step (i) using 0.01 to 0.025 N alkali solution to form an eluate containing sGAG, and wherein prior to precipitation in step (j), the alkali solution is neutralized to a pH of 7.

11. The method of claim 1, wherein in step (i) sGAG is removed using a solution of 1.5 N sodium chloride in 0.8 acetic acid.

12. The method of claim 1, wherein in step (i) sGAG is removed with a solution of 0.02 M NaOH.

* * * * *